US008546606B2

(12) United States Patent  
Brodhagen et al.

(10) Patent No.: US 8,546,606 B2  
(45) Date of Patent: Oct. 1, 2013

(54) METHOD FOR PRODUCING POLYISOCYANATES

(75) Inventors: Andreas Brodhagen, Bierbeeg (BE); Martin Sohn, Mannheim (DE); Filip Nevejans, St. Gillis-Waas (BE); Eckhard Stroefer, Mannheim (DE); Andreas Woelfert, Bad Rappenau (DE); Steffen Oehlenschlaeger, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1147 days.

(21) Appl. No.: 10/546,890

(22) PCT Filed: Feb. 20, 2004

(86) PCT No.: PCT/EP2004/001673  
§ 371 (c)(1),  
(2), (4) Date: Aug. 24, 2005

(87) PCT Pub. No.: WO2004/080587  
PCT Pub. Date: Sep. 23, 2004

(65) Prior Publication Data  
US 2006/0223966 A1 Oct. 5, 2006

(30) Foreign Application Priority Data

Mar. 11, 2003 (DE) .................... 103 10 888

(51) Int. Cl.  
*C07C 249/00* (2006.01)

(52) U.S. Cl.  
USPC .................. 560/347; 252/182.13; 252/182.29

(58) Field of Classification Search  
USPC ............ 560/347; 422/197, 201; 252/182.13, 252/182.29  
See application file for complete search history.

(56) References Cited

U.S. PATENT DOCUMENTS

| 3,544,612 | A |   | 12/1970 | Alheritiere |
|-----------|---|---|---------|-------------|
| 3,595,846 | A | * | 7/1971  | Rouzier ..................... 526/64 |
| 3,829,458 | A |   | 8/1974  | Horn et al. |
| 4,419,295 | A |   | 12/1983 | Hennig et al. |
| 4,851,570 | A | * | 7/1989  | Zaby et al. ................. 560/347 |
| 5,779,994 | A |   | 7/1998  | Kuepper et al. |

FOREIGN PATENT DOCUMENTS

| DE | 949 228    | 9/1956  |
| DE | 1 593 412  | 8/1970  |
| DE | 2 112 181  | 10/1972 |
| DE | 27 47 524  | 5/1978  |
| DE | 31 21 036  | 12/1982 |
| EP | 0 322 647  | 7/1989  |
| EP | 0 716 079  | 6/1996  |

OTHER PUBLICATIONS

Grant, Roger; Grant, Claire, Chemical Dictionary, 5th Ed. McGraw-Hill Book Company, New York, NY. 1987. p. 239.*

* cited by examiner

*Primary Examiner* — Michael L Leonard  
(74) *Attorney, Agent, or Firm* — Oblon, Spivak, McClelland, Maier & Neustadt, L.L.P.

(57) ABSTRACT

The invention relates to a process for preparing polyisocyanates by reacting primary amines with phosgene, which comprises the steps  
a) mixing the amine with the phosgene,  
b) reacting the amine with the phosgene in a residence reactor and, if desired,  
c) transferring the output from the reactor of step b) into a distillation column, wherein the residence reactor in step b) is configured as a tube reactor.

18 Claims, No Drawings

METHOD FOR PRODUCING POLYISOCYANATES

The present invention relates to a novel process for preparing isocyanates by reacting primary amines with phosgene.

Polyisocyanates are prepared in large quantities and are employed mainly as starting materials for the preparation of polyurethanes. They are usually prepared by reacting the corresponding amines with phosgene.

In general, the continuous variant of this process is carried out in two stages. In the first stage, viz. the phosgenation, the amine is reacted with phosgene to form the carbamoyl chloride and hydrogen chloride and, in a parallel reaction, to form the amine hydrochloride. The reaction between amine and phosgene is very fast, strongly exothermic and proceeds even at very low temperatures. To minimize formation of by-products and solids, amine and phosgene, if desired in admixture with an organic solvent, have to be mixed quickly. The first phosgenation stage is therefore generally carried out in a mixing apparatus, preferably a nozzle. The second stage of the phosgenation encompasses both the decomposition of the carbamoyl chloride to form the desired isocyanate and hydrogen chloride and the phosgenation of the amine hydrochloride to form the carbamoyl chloride. The temperature in the second phosgenation stage is generally higher than that in the first. Many reactors have been developed for the second stage.

It is known that improved results can be obtained in the phosgenation at a given residence time by narrowing the residence time distribution. Various processes for preparing isocyanates by reacting amines with phosgene in the liquid phase while maintaining a narrow residence time distribution have therefore been described in the literature. A narrow residence time distribution can be achieved, for example, by use of a cascade of stirred vessels or by use of a tube reactor.

The simplest possibility of use of a cascade as apparatus combination having the residence time characteristics of a tube reactor is phosgenation in a cascade of stirred vessels, as described in DE 844 896. A disadvantage here is the use of moving parts. In the case of apparatuses in which phosgene is present, the use of moving parts should be avoided for safety reasons, particularly because of the risk of leaks at points where a shaft passes through a wall.

EP 322,647 describes a phosgenation tower having perforated plates as internals for the continuous preparation of monoisocyanates or polyisocyanates. The perforated plates as internals are intended to achieve cascading of the flow, which leads to a narrower residence time distribution. A disadvantage is the tendency of the perforated plates to become blocked in long-term operation.

EP 716,079 describes the reaction of amine and phosgene in a bubble column or a loop reactor as tube reactor with a downstream reactor for the reaction of amine hydrochloride and recirculation of the reaction mixture. A disadvantage of this process is that a low space-time yield is obtained because of the large quantities of material recirculated.

DE 2,747,524 describes phosgenation in a tube reactor whose wall is heated, particularly in the region after the mixing-in of amine and phosgene, so that the carbamoyl chloride formed should not deposit on the tube wall.

DE 2,112,181 describes phosgenation in a packed tube reactor in cocurrent, with the flow in the tube reactor being maintained in the transition regime between laminar and pulsating flow and part of the finished reaction solution being recirculated to the tube reactor. A disadvantage is the tendency of the reactor to become blocked by deposits of solids on the packing elements.

DE 2,058,032 describes a two-stage phosgenation in which the hot phosgenation is carried out in a horizontal tube with a built-in stirrer, for example a helical stirrer or transport screw, and facilities for taking off gas at the side. Here too, the use of moving parts is a disadvantage.

DE 949,228 describes a process for the continuous preparation of monocyclic aromatic diisocyanates. In the continuous process for preparing isocyanates from primary amines using phosgene in a two-stage cold-hot phosgenation, the hot phosgenation is carried out in a vertical or slanting tube or tower with addition of gaseous phosgene. However, the poor space-time yield of the cold-hot phosgenation is a drawback.

DE 3,121,036 describes a continuous process for preparing isocyanates, in which a constant temperature is employed in a combination of mixing nozzle and tube reactor. A disadvantage of this process is that the volume of the tube reactor is very large because intermediate degassing is omitted.

U.S. Pat. No. 3,544,612 describes a process in which isocyanate is prepared by phosgenation of amine hydrochloride in countercurrent in a tube reactor or a column, with the hydrochloride dispersion being added at the top and the phosgene solution being introduced at the bottom. To improve mass transfer between phosgene solution and hydrochloride dispersion, inert packing or plates are recommended. Disadvantages of this process are, in particular, the tendency of the internals to become blocked and the long phosgenation time required by the amine hydrochloride.

DE 1,593,412 describes a process for preparing isocyanates at superatmospheric pressures in a distillation column. The process is preferably carried out in a distillation column, with the feed from the cold phosgenation being introduced in the upper third of the column. Hydrogen chloride and sometimes phosgene are obtained at the top of the column. The crude isocynate solution is taken off at the bottom. Recommended column internals are packing elements (Raschig rings). Disadvantages of the process are the backmixed bottom circulation and the tendency of the packing elements to become blocked. When the process is carried out in a tray column, the large unutilized gas volumes which prevent a compact process design represent a further disadvantage.

U.S. Pat. No. 3,829,458 describes a packed tube reactor for reacting amine and phosgene in which the reactants flow in cocurrent through the reactor and the flow in the reactor is in the transition state between laminar and turbulent. A drawback is that the use of packing in the phosgenation reactor is excessively susceptible to the presence of solids.

DD 300 168 describes a horizontal tube reactor with injection of amine and phosgene, in which the phosgene is introduced above and below the amine. A drawback is that the simple horizontal construction without further measures results in a high proportion of gas in the tube and a relatively broad residence time distribution. This gives a relatively poor space-time yield and thus a not very compact construction.

It is an object of the present invention to provide a process for preparing isocyanates which allows the resulting reaction(s) to be carried out with high selectivity and a high space-time yield, so that the process can be designed in a compact fashion and can be operated very reliably in respect of blockages.

We have found that this object is achieved by a process for preparing polyisocyanates by reacting primary amines with phosgene, which comprises the steps
 a) mixing the amine with the phosgene,
 b) reacting the amine with the phosgene in a residence reactor and, if desired, c) transferring the output from the reactor of step b) into a distillation column, wherein the residence reactor in step b) is configured as a tube reactor.

For the configuration of the tube reactor, there are in principle 4 possibilities.

1. The tube reactor is essentially vertical and the flow through it is from the bottom upward. Advantages of this configuration are the cocurrent flow of bubbles and liquid and the relatively stable operation without impediment to flow and spitting. A disadvantage is that the flow has to be sufficiently fast to prevent solids occurring in the phosgenation from sedimenting. This gives a relatively narrow operating range for proper operation of the tube reactor. For example, at part load, the turbulence would be too low. The solids would sediment and the reactor would become blocked.
2. The tube reactor is essentially vertical and flow though it is from the top downward. An advantage of this configuration is that the solids cannot sediment. A disadvantage is that gas and liquid are conveyed in countercurrent. As a result, the liquid flow can become impeded by large coherent gas bubbles. The apparatus then operates in a, pulsating fashion, which represents an unstable, undesirable mode of operation.
3. Homogeneous flow is generated by selecting a narrow tube diameter. This results in the velocity of liquid and gas being increased to such a rate that the flow is homogenized. Flow of gas and liquid is distributed uniformly over the cross section without formation of a laminar structure or of surges. For the purposes of the present invention, the term "surge" refers to a wave of liquid in which, in the case of a two-phase system, the liquid takes up the entire cross section of the tube. This parts the gas phase in the reactor. An advantage of this embodiment is that sedimentation of solids does not occur. A disadvantage is that, owing to the high flow velocity, very great tube lengths are required in order to achieve the desired residence time. Furthermore, the pressure drop increases linearly with the tube length and proportionally to the square of the increase in the flow velocity which is desired per se. If deposits on the wall are formed despite the high velocity, cleaning of the narrow tube is more difficult than in the case of a larger cross section.
4. The tube reactor is essentially horizontal. An advantage of this embodiment is that sedimentation of solids is prevented even at very low flow velocities. A disadvantage is that unstable phase separation can occur, which can lead to surges in the liquid, particularly in the case of deflections. Surges, which move at a number of times the mean flow velocity, considerably increase mechanical stresses on the apparatus. This can in long-term operation lead to damage to the reactor and components connected thereto and consequently result in escape of product into the environment. Furthermore, the high velocity of the surges compared to the mean flow velocity broadens the residence time distribution. According to the present observations which have led to the present invention, this leads to a reduction in the product quality. Since the forward movement of the gas phase is hindered by the surges, a low slip and thus a high proportion by volume of gas is obtained in the region of surge flow. This leads to a not very compact and thus expensive construction.

A further object of the invention is therefore to configure the tube reactor so that a uniform residence time distribution of the reaction mixture is achieved and the occurrence of surges in the reactor can be prevented.

We have found that this object is achieved by the tube reactor comprising one or more horizontal and/or vertical segments which are connected to one another by sections which have a diameter less than the diameter of the narrowest horizontal or vertical segment.

The present invention therefore also provides a process for preparing polyisocyanates by reacting primary amines with phosgene, which comprises the steps a) mixing the amine with the phosgene,
b) reacting the amine with the phosgene in a residence reactor and, if desired,
c) transferring the output from the reactor of step b) into a distillation column wherein the tube reactor in step b) comprises one or more horizontal and/or vertical segments which are connected to one another by sections which have a diameter less than the diameter of the narrowest horizontal or vertical segment, wherein the residence reactor in step b) is configured as a tube reactor.

The present invention further provides for the use of a tube reactor comprising one or more horizontal and/or vertical segments which are connected to one another by sections which have a diameter less than the diameter of the narrowest horizontal or vertical segment for preparing polyisocyanates by reacting primary amines with phosgene.

The tube reactor usually has no internals.

In one embodiment of the invention, the tube reactor can have a linear construction, i.e. it comprises a plurality of horizontal segments which are connected to one another by horizontal connecting sections. This embodiment is very simple, but it has the disadvantage that use of a large number of horizontal segments results in a very long tube reactor, which leads to a not very compact configuration of the plant.

For this reason, the connecting sections are configured as pipe bends in a preferred embodiment of the invention. In this embodiment, the reactor can comprise a plurality of essentially horizontal segments.

In a further, preferred embodiment of the tube reactor, essentially horizontal sections are combined with essentially vertical sections so that, for example, the requirements of the reaction are achieved while overcoming a large distance between the apparatuses for the reaction steps a) and c). The individual segments are connected at their ends via pipe bends. The segments can be arranged next to and above one another in order to achieve a particularly compact construction.

Making the diameter of the connecting sections smaller than the diameter of the tube segments which they connect enables an increase in the flow velocity and, in the pipe bend only, the pressure drop per meter of pipe to be achieved. This leads to homogenization of the flow. The backing up of liquid upstream of the bends is prevented and the main cause of surges is thus eliminated.

To achieve a sufficient increase in the velocity, preference is given to the diameter of the connecting sections to be less than or equal to 0.95 times, preferably 0.75 times and particularly preferably 0.5 times, the diameter of the segment having the smallest diameter.

It has also been found that above a particular length of tube between two bends, surge flow arises directly from the existing wave or laminar flow. For occurrence of surges in the essentially horizontal segments between the bends to be prevented reliably, the length of the segments should be less than 250 times, preferably less than 100 times, particularly preferably less than or equal to 50 times, their diameter.

When essentially horizontal segments are used, their inclination should be in the range from −10° to +10°, preferably in the range from −5° to +5° and particularly preferably in the range from −3° to +3°. In this way it can be ensured that the tube reactor can be emptied completely before carrying out repairs.

The medium flowing through the tube reactor is usually a mixture of a gaseous and/or vapor phase and a liquid. However, it is in principle also possible for the proportion of liquid to be increased by increasing the system pressure up to the limiting case of single-phase liquid flow.

If necessary, the tube reactor can be heatable/coolable. Temperature control can in this case be achieved by means of heating/cooling of the reactor wall or internal heat exchange surfaces.

An advantage of the tube reactor used according to the present invention is that no internals of any sort are required in the tubes to achieve unform flow without surges. By this means, the formation of deposits and blockages is reduced. Should cleaning of the tube nevertheless be necessary, this can be carried out much more easily than in the case of construction types containing internals. Owing to the simple design, capital costs can also be saved in comparison with other constructions.

The tube reactor used according to the present invention and having the structural features described in more detail above is thus also suitable for other reactions in which a gas phase and a liquid phase are simultaneously present. The invention therefore also provides a tube reactor comprising one or more horizontal and/or vertical segments which are connected to one another by sections which have a diameter less than the diameter of the narrowest horizontal or vertical segment. The diameter of the connecting sections is preferably less than or equal to 0.95 times, preferably 0.75 times and particularly preferably 0.5 times, the diameter of the segment having the smallest diameter. It is also preferred that the length of the segments is less than 250 times, preferably less than 100 times and particularly preferably less than or equal to 50 times, their diameter.

To achieve a higher final conversion in the process of the present invention, it can be useful for the output from the tube reactor to be fed to a distillation column to allow an after-reaction to occur. In this distillation column, the liquid phase is passed through the column from the top downward and the gas phase is passed through the column from the bottom upward.

The reduction in the total reaction volume allows the plant to be made significantly more compact. In view of the hazards associated with the phosgene handled in the plant, this represents a considerable increase in the safety of the plant and at the same time a reduction in the capital costs.

The reaction of the amine with the phosgene preferably takes place at from 60 to 200° C. and at absolute pressures of from 0.9 bar to 400 bar, with the molar ratio of phosgene to amino groups used being, in particular, from 15:1 to 1:1.

The residence time of the reaction mixture in the tube reactor is, depending on the amine used, from 5 s to 3 h. The residence time is preferably in the range from 5 s to 1000 s, preferably in the range from 20 s to 500 s, particularly preferably in the range from 25 s to 200 s.

The mixing of the reactants in step a) of the process of the present invention is preferably carried out in a mixing apparatus in which the stream of reaction mixture passed through the mixing apparatus is subjected to high turbulent shear. It is preferably a rotary mixing apparatus, a mixing pump or a mixing nozzle, particularly preferably a mixing nozzle, and is installed upstream of the tube reactor. Such nozzles are described, for example, in DD 300 168, WO 01/91898 and WO 02/02217.

The residence time in step b) is usually sufficient to ensure complete conversion of the reaction mixture into the isocyanate. However, it can be advantageous to feed the reaction mixture leaving the tube reactor into an after-reactor, in particular a reaction column c), to complete the reaction. Such columns are described, for example, in WO 99/54285.

In this after-reactor, complete decomposition of carbamoyl chloride and amine hydrochloride still present in the reaction mixture occurs. The conditions in the after-reactor should be chosen so that complete reaction is ensured. When a column is used, it is advantageous for the liquid phase, e.g. phosgene, isocyanate and solvent, to be passed through the column from the top downward and the low boilers, e.g. phosgene and hydrogen chloride, to be passed through it from the bottom upward.

A section having the same diameter as the connecting sections can be installed between the tube reactor of step b) and the after-reactor of step c). It can also be advantageous to install a regulating valve between tube reactor and after-reactor in order to ensure uniform entry of product into the after-reactor.

The process of the present invention can be carried out using any primary amine or a mixture of two or more such amines. Examples are methylenedi(phenylamine) (individual isomers, mixtures of isomers and/or oligomers), toluenediamine, n-pentylamine, 6-methyl-2-heptanamine, cyclopentylamine, R,S-1-phenylethylamine, 1-methyl-3-phenylpropylamine, 2,6-xylidine, 2-dimethylaminoethylamine, 2-diisopropylaminoethylamine, C11-neodiamine, isophoronediamine, 1,6-hexamethylenediamine, naphthylenediamine, bis(3,3'-aminophenyl)sulphone and 4-aminomethyl-1,8-octanediamine. Preference is given to using aromatic amines, in particular toluenediamine and diaminodiphenylmethane or its higher homologues.

The process of the present invention is in general suitable for preparing any isocyanates. The process can be employed particularly advantageously for preparing methylenedi(phenyl isocyanate) (MDI) and tolylene diisocyanate (TDI).

In the process of the present invention, the starting materials can be dissolved in an inert solvent. These inert solvents are usually organic solvents which can be used individually or in admixture. Preference is given to chlorobenzene, dichlorobenzene, trichlorobenzene, toluene, hexane, diethyl isophthalate (DEIP), tetrahydrofuran (THF), dimethylformamide (DMF), benzene and mixtures thereof. Particular preference is given to chlorobenzene. In a particular embodiment of the process of the present invention, the isocyanate prepared in the process can also be used as solvent, as described, for example, in WO 96/16028.

After the reaction, the product mixture is preferably separated into isocyanate(s), solvent, phosgene and hydrogen chloride by means of rectification. Small amounts of by-products which remain in the isocyanate can be separated from the desired isocyanate by means of additional rectification or crystallization.

The isocyanates prepared by the process of the present invention can be used, in particular, for the preparation of polyurethanes. For this purpose, they are reacted in a known manner with compounds having at least two hydrogen atoms which are reactive toward isocyanate groups.

The invention is illustrated by the following examples.

EXAMPLES

In an experimental apparatus, a liquid/gas mixture was passed through a length of tube which was made up of two straight horizontal tubes (DN 200, length in each case 5 m)

connected to one another via a 180° pipe bend. The outlet of the length of tube was 1.2 m higher than the inlet. The height difference was overcome mainly in the pipe bend. Pipe bends used were a) a bend whose diameter is the same as the diameter of the straight segments of the reactor (DN 200), and
b) a bend having a diameter which is half that of the straight tubes (DN 100).

In both arrangements, the volume flow of liquid was varied in the range 20 m$^3$/h-60 m$^3$/h and the volume flow of gas was varied in the range 20 m$^3$/h-200 m$^3$/h. In each experiment, the type of flow established was observed and the pressure difference over the pipe bends was measured.

a) Experiments in the arrangement with pipe bend DN 200:
The flow in the upper tube was virtually exclusively surge flow at all liquid throughputs and gas throughputs. This was obviously caused by inhomogeneous flow through the pipe bend. The pressure drop over the bend was 0.2 bar at 20 m$^3$/h of liquid and 20 m$^3$/h of gas, and rose with increasing volume flows to 0.5 bar at 60 m$^3$/h of liquid and 200 m$^3$/h of gas.

b) Experiments in the arrangement with pipe bend DN 100:
Above a volume flow of liquid of 40 m$^3$/h, no liquid surges occurred. The type of flow observed was wave flow. The pressure drop over the pipe bend was 0.2 bar at 20 m$^3$/h of liquid and 20 m$^3$/h of gas, and rose with increasing volume flows to 0.6 bar at 60 m$^3$/h of liquid and 200 m$^3$/h of gas. The higher pressure drop compared to case a) thus contributed to mixing of the phases in the bend and thus to homogenization of the flow.

We claim:

1. A process for preparing polyisocyanates by reacting primary amines with phosgene, which comprises the steps
a) mixing an amine with phosgene,
b) reacting said amine with said phosgene in a residence reactor
wherein the residence reactor in step b) is configured as a tube reactor comprising horizontal segments, vertical segments, or a combination thereof, which are connected to one another by sections which have a diameter less than the diameter of the narrowest horizontal or vertical segment and
wherein said phosgene and said amine comprise a flowing medium comprises a mixture of a gaseous and/or vapor phase and a liquid, wherein said gaseous and/or vapor phase comprises phosgene and wherein said amine and phosgene are reacted at a temperature of from 60 to 200° C. and an absolute pressure of from 0.9 to 400 bar.

2. The process as claimed in claim 1, wherein the connecting sections are configured as pipe bends.

3. The process as claimed in claim 1, wherein the diameter of the connecting sections is less than or equal to a value of 0.95 times the smallest diameter of the horizontal segments, the vertical segments, or a combination thereof.

4. The process as claimed in claim 1, wherein the diameter of the connecting sections is less than or equal to a value of 0.75 times the smallest diameter of the horizontal segments, the vertical segments, or a combination thereof.

5. The process as claimed in claim 1, wherein the diameter of the connecting sections is less than or equal to a value of 0.5 times the smallest diameter of the horizontal segments, the vertical segments, or a combination thereof.

6. The process as claimed in claim 1, wherein the length of the horizontal segments, the vertical segments, or a combination thereof, is less than 250 times, the diameter of the tube.

7. The process of claim 1, wherein the residence time of the liquid in step b) is in the range from 5 s to 1000 s.

8. The process of claim 1, wherein the residence time of the liquid in step b) is in the range from 20 s to 500 s.

9. The process of claim 1 wherein the residence time of the liquid in step b) is in the range from 25 s to 200 s.

10. The process of claim 1, wherein the horizontal segments have an inclination to the horizontal in the range from −10° to +10°.

11. The process of claim 1, wherein the amine is selected from the group consisting of methylenedi(phenylamine), its higher homologues, toluenediamine, n-pentylamine, 6-methyl-2-heptanamine, cyclopentylamine, R,S-1-phenylethylamine, 1-methyl-3-phenylpropylamine, 2,6-xylidine, 2-dimethylaminoethylamine, 2-diisopropylaminoethylamine, C11-neodiamine, isophoronediamine, 1,6-hexamethylenediamine, naphthylenediamine, bis(3,3'-aminophenyl)sulfone and 4-aminomethyl-1,8-octanediamine.

12. A method for making isocyanates comprising reacting a primary amine and phosgene in a tube reactor comprising horizontal segments, vertical segments, or a combination thereof, which are connected to one another by sections which have a diameter less than the diameter of the narrowest horizontal or vertical segment
wherein said phosgene and said primary amine comprise a flowing medium comprises a mixture of a gaseous and/or vapor phase and a liquid, wherein said gaseous and/or vapor phase comprises phosgene.

13. The process as claimed in claim 1, wherein the length of the horizontal segments, the vertical segments, or a combination thereof, is less than 100 times the diameter of the tube.

14. The process as claimed in claim 1, wherein the length of the horizontal segments, the vertical segments, or a combination thereof, is less than 50 times the diameter of the tube.

15. The process of claim 1, wherein the horizontal segments have an inclination to the horizontal in the range from −5° to +5°.

16. The process of claim 1, wherein the horizontal segments have an inclination to the horizontal in the range from −3° to +3°.

17. The process of claim 1 further comprising,
c) transferring an output from the reactor of step b) into a distillation column.

18. The process of claim 1, wherein sad tube reactor has no internals.

* * * * *